(12) United States Patent
Moon et al.

(10) Patent No.: US 12,377,445 B2
(45) Date of Patent: Aug. 5, 2025

(54) FOOD PROCESSING SYSTEM CAPABLE OF CLEANING-IN-PLACE AND CLEANING METHOD OF SAME

(71) Applicant: CJ CHEILJEDANG CORPORATION, Seoul (KR)

(72) Inventors: Sung Yang Moon, Suwon-si (KR); Doo Seong Jeong, Suwon-si (KR); Gun Woo Lee, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 18/027,620

(22) PCT Filed: Aug. 26, 2021

(86) PCT No.: PCT/KR2021/011484
§ 371 (c)(1),
(2) Date: Mar. 21, 2023

(87) PCT Pub. No.: WO2022/108059
PCT Pub. Date: May 27, 2022

(65) Prior Publication Data
US 2023/0381828 A1    Nov. 30, 2023

(30) Foreign Application Priority Data
Nov. 17, 2020  (KR) ........................ 10-2020-0154069

(51) Int. Cl.
*B08B 3/02*     (2006.01)
*A47J 27/04*    (2006.01)
(Continued)

(52) U.S. Cl.
CPC .............. *B08B 3/024* (2013.01); *A47J 27/04* (2013.01); *A61L 2/18* (2013.01); *A61L 2/24* (2013.01);
(Continued)

(58) Field of Classification Search
CPC .................................................... B08B 3/024
See application file for complete search history.

(56) References Cited

U.S. PATENT DOCUMENTS

| 6,014,994 A | 1/2000 | Schmidt |
| 2007/0170040 A1 | 7/2007 | Handy |

(Continued)

FOREIGN PATENT DOCUMENTS

| EP | 4230057 A1 | 8/2023 |
| JP | S61-113455 A | 5/1986 |

(Continued)

OTHER PUBLICATIONS

Office Action issued Mar. 5, 2024 for Japanese Patent Application No. 2023-524739.

(Continued)

*Primary Examiner* — Jason Y Ko
(74) *Attorney, Agent, or Firm* — Morgan, Lewis & Bockius LLP

(57) ABSTRACT

The food processing system according to the present invention comprises: a transport unit for continuously transporting food; a processing unit through which the transport unit passes and which is provided with an internal space for processing food transported by the transport unit; and a cleaning unit provided with a plurality of nozzles for spraying the internal space with liquid, either cleaning material or cleaning water, to clean the interior of the processing unit, and a liquid supply module for selectively supplying the plurality of nozzles with either the cleaning material or cleaning water.

19 Claims, 12 Drawing Sheets

(51) Int. Cl.
*A61L 2/18* (2006.01)
*A61L 2/24* (2006.01)
*B05B 1/14* (2006.01)
*B05B 3/02* (2006.01)
*B08B 3/00* (2006.01)

(52) U.S. Cl.
CPC ................ *B05B 1/14* (2013.01); *B05B 3/02* (2013.01); *B08B 3/003* (2013.01); *A61L 2202/14* (2013.01); *A61L 2202/15* (2013.01); *A61L 2202/17* (2013.01); *B08B 2203/027* (2013.01); *B08B 2230/01* (2013.01)

(56) References Cited

U.S. PATENT DOCUMENTS

| | | |
|---|---|---|
| 2017/0028449 A1 | 2/2017 | Fernholz et al. |
| 2017/0362037 A1 | 12/2017 | Handy |
| 2018/0236117 A1 | 8/2018 | Agmont E Silva |
| 2022/0134393 A1 | 5/2022 | Gorni et al. |
| 2023/0301331 A1 | 9/2023 | Moon et al. |

FOREIGN PATENT DOCUMENTS

| | | |
|---|---|---|
| JP | H08-173925 A | 7/1996 |
| JP | H08-308546 A | 11/1998 |
| JP | H11-37624 A | 2/1999 |
| JP | H11-037625 A | 2/1999 |
| JP | 2867218 B2 | 3/1999 |
| JP | 2004-8944 A | 1/2004 |
| JP | 4450354 B2 | 4/2010 |
| JP | 6283926 B2 | 2/2018 |
| JP | 2018-526200 A | 9/2018 |
| KR | 10-0634375 B1 | 10/2006 |
| KR | 10-1058419 B1 | 8/2011 |
| KR | 10-1323837 B1 | 10/2013 |
| KR | 10-2015-0009878 A | 1/2015 |
| KR | 10-2020-0033827 A | 3/2020 |
| KR | 10-2020-0037541 A | 4/2020 |
| KR | 10-2261583 B1 | 6/2021 |
| WO | 2020/163699 A1 | 8/2020 |

OTHER PUBLICATIONS

International Search Report issued in corresponding International Patent Application No. PCT/KR2021/011484 dated Nov. 10, 2021.
Partial Supplementary European Search Report issued in corresponding European Patent Application No. 21894832.1, dated Oct. 17, 2024.
Extended European Search Report issued in corresponding European Patent Application No. 21894832.1, dated Mar. 31, 2025.
Pretrial Reexamination Report issued in corresponding Japanese Patent Application No. 2023-524739, dated Apr. 1, 2025.

FOOD PROCESSING SYSTEM CAPABLE OF CLEANING-IN-PLACE AND CLEANING METHOD OF SAME

TECHNICAL FIELD

The present invention relates to a food processing system capable of cleaning-in-place and a cleaning method of the same.

BACKGROUND ART

A system for use in production of frozen foods, particularly dumplings, is configured so that appropriate processing such as heat processing, is performed on the foods continuously passing through the system to cook the foods and appropriate post-processing such as sterilization or freezing, is carried out. In food processing, residues of the foods may remain or materials used for the processing may remain in a device. Such residues need to be cleaned and removed periodically in order to maintain quality of the produced foods.

A worker may be put for the cleaning of the system. When the device is cleaned manually through worker input, the worker may be injured. Thus, a temperature of a portion at which steaming is carried out needs to be sufficiently decreased to be similar to the room temperature, and a temperature of a portion at which freezing is carried out needs to be sufficiently increased to be similar to the room temperature. Since the food processing needs to be re-performed normally after the cleaning is carried out, the temperature of the portion at which the steaming is carried out needs to be increased, and the temperature of the portion at which the freezing is carried out needs to be decreased. That is, sufficient time and energy are required to adjust the temperature of each of the parts of the device before and after the worker input.

The system may have a height that is much greater than an average adult height. In this case, the worker has a risk of safety-related accidents caused by high place work.

DISCLOSURE OF THE INVENTION

Technical Problem

This present invention has been devised to solve the problems as above and an object of the present invention is to provide a food processing system capable of cleaning-in-place without worker input, and a cleaning method of the same.

Technical Solution

A food processing system according to an embodiment of the present invention includes: a transport unit provided to continuously transport foods; a processing unit through which the transport unit passes and which defines an internal space in which the foods transported by the transport unit are processed; and a cleaning unit including a plurality of nozzles that inject liquid, which is any one of cleaning material and cleaning water, into the internal space in order to clean the interior of the processing unit, and a liquid supply module that selectively supplies any one of the cleaning material and the cleaning water to the plurality of nozzles.

A method for cleaning a food processing system, which includes a processing unit that defines an internal space in which continuously transported foods are processed, according to an embodiment of the present invention includes: injecting cleaning water into the internal space for removal of residues present in the internal space; injecting cleaning foam into the internal space; injecting the cleaning water into the internal space for removal of the cleaning foam; injecting a sanitizer into the internal space; and injecting the cleaning water into the internal space for removal of the sanitizer.

Advantageous Effects

Accordingly, the cleaning-in-place of the food processing system is possible even without the worker input and thus, the time required for the cleaning is reduced and the worker's risk of injuries is reduced.

MODE FOR CARRYING OUT THE INVENTION

Figure 1:
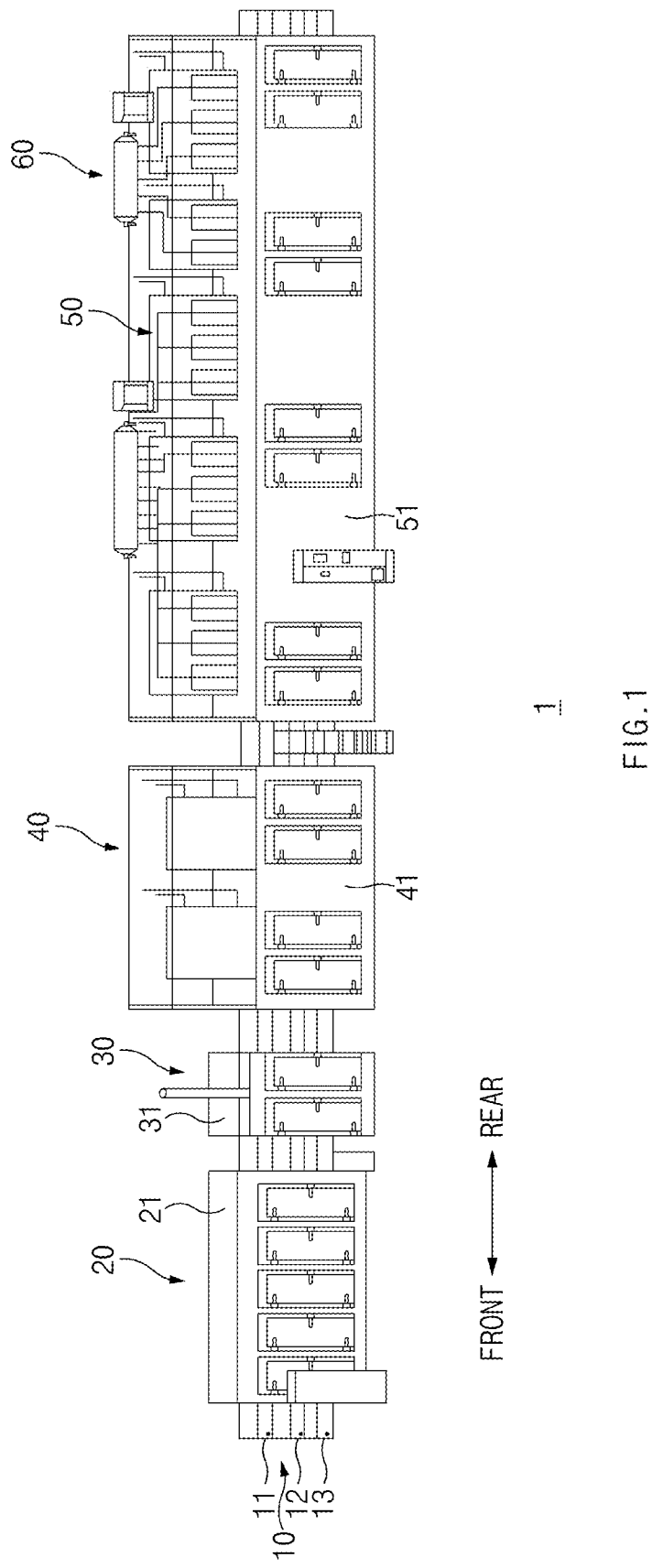
FIG. 1 is a perspective view of a food processing system according to an embodiment of the present invention.

The present application claims the benefit of the priority of Korean Patent Application No. 10-2020-0154069, filed on Nov. 17, 2020, which is hereby incorporated by reference in its entirety.

Hereinafter, some embodiments of the present invention will now be described in detail with reference to the accompanying drawings. Note that like components in the drawings are designated by like reference numerals as far as possible even if they are shown in different drawings. In the following description of the present invention, a detailed description of known functions and configurations incorporated herein will be omitted to avoid making the subject matter of the present invention unclear.

In the description of the elements of the present invention, the terms "first", "second", "A", "B", "(a)", and "(b)" may be used. However, since the terms are used only to distinguish an element from another, the essence, sequence, and order of the elements are not limited by them. When it is described that an element is "coupled to", "engaged with", or "connected to" another element, it should be understood that the element may be directly coupled or connected to the other element but still another element may be "coupled to", "engaged with", or "connected to" the other element between them.

Figure 2:
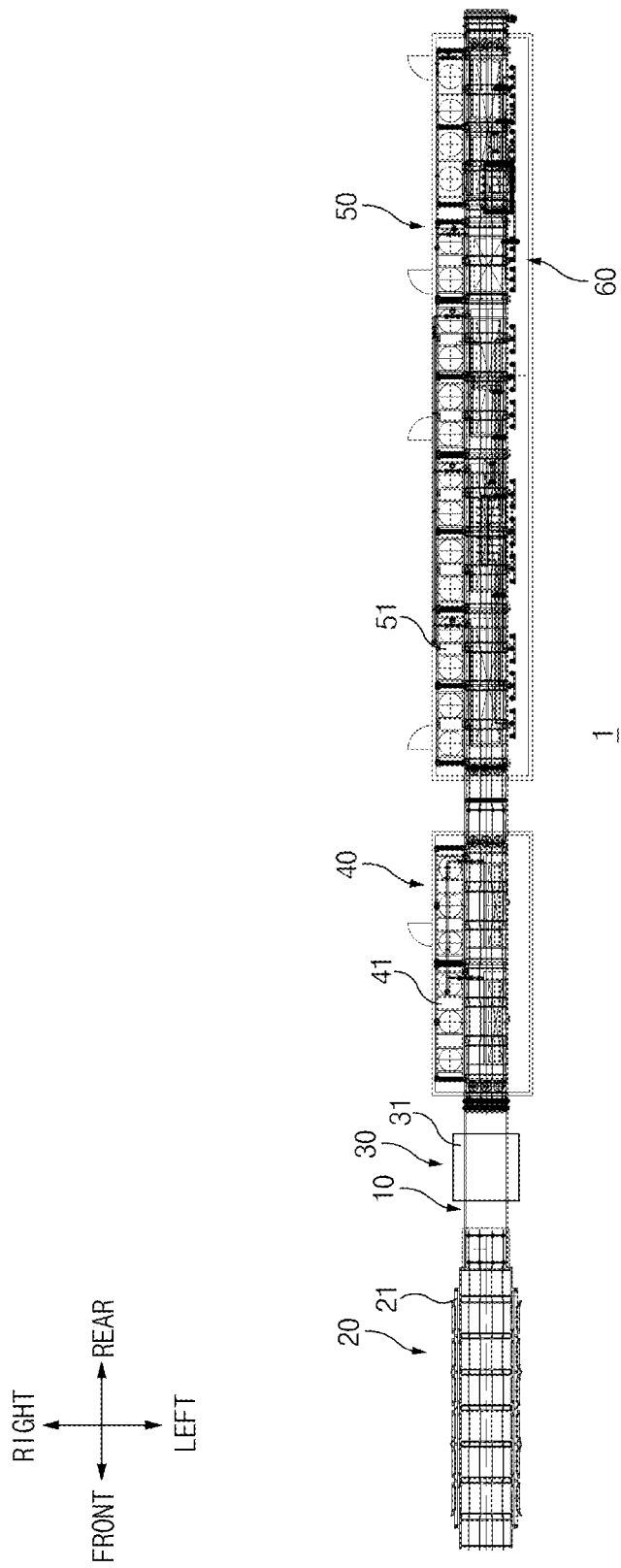
FIG. 2 is a view of a food processing system when viewed downward from top in a state in which an inner structure of the food processing system is exposed according to an embodiment of the present invention.
Figure 3:
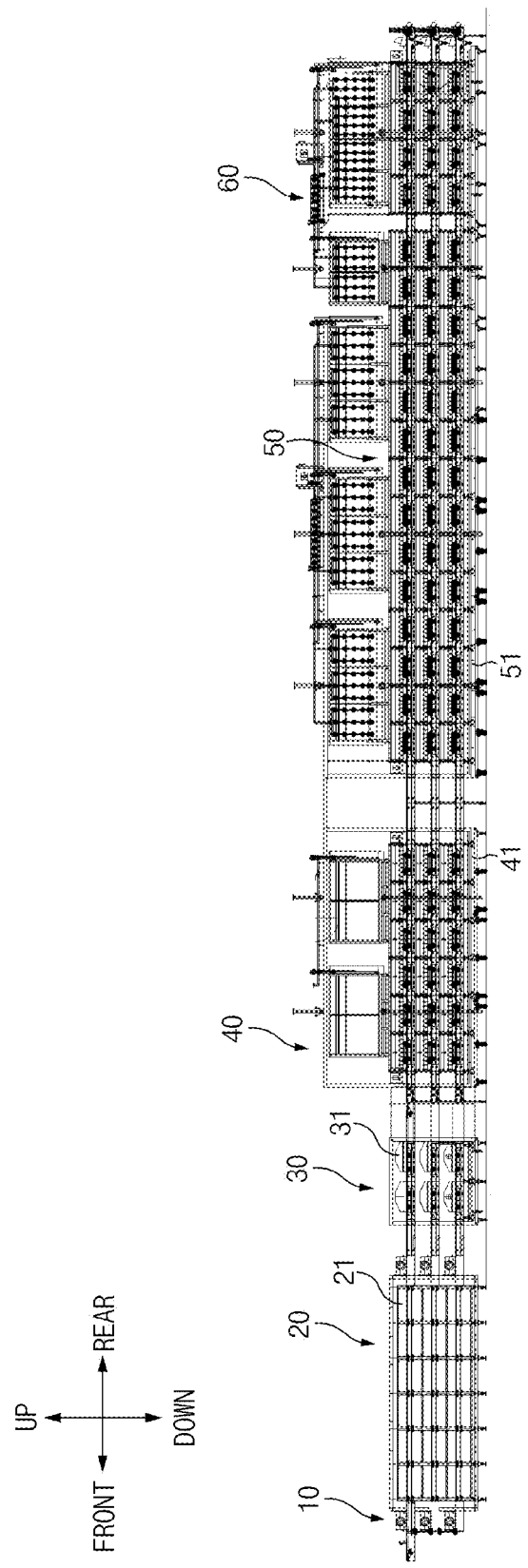
FIG. 3 is a view of a food processing system when viewed from a side in a state in which an inner structure of the food processing system is exposed according to an embodiment of the present invention.
Figure 4:
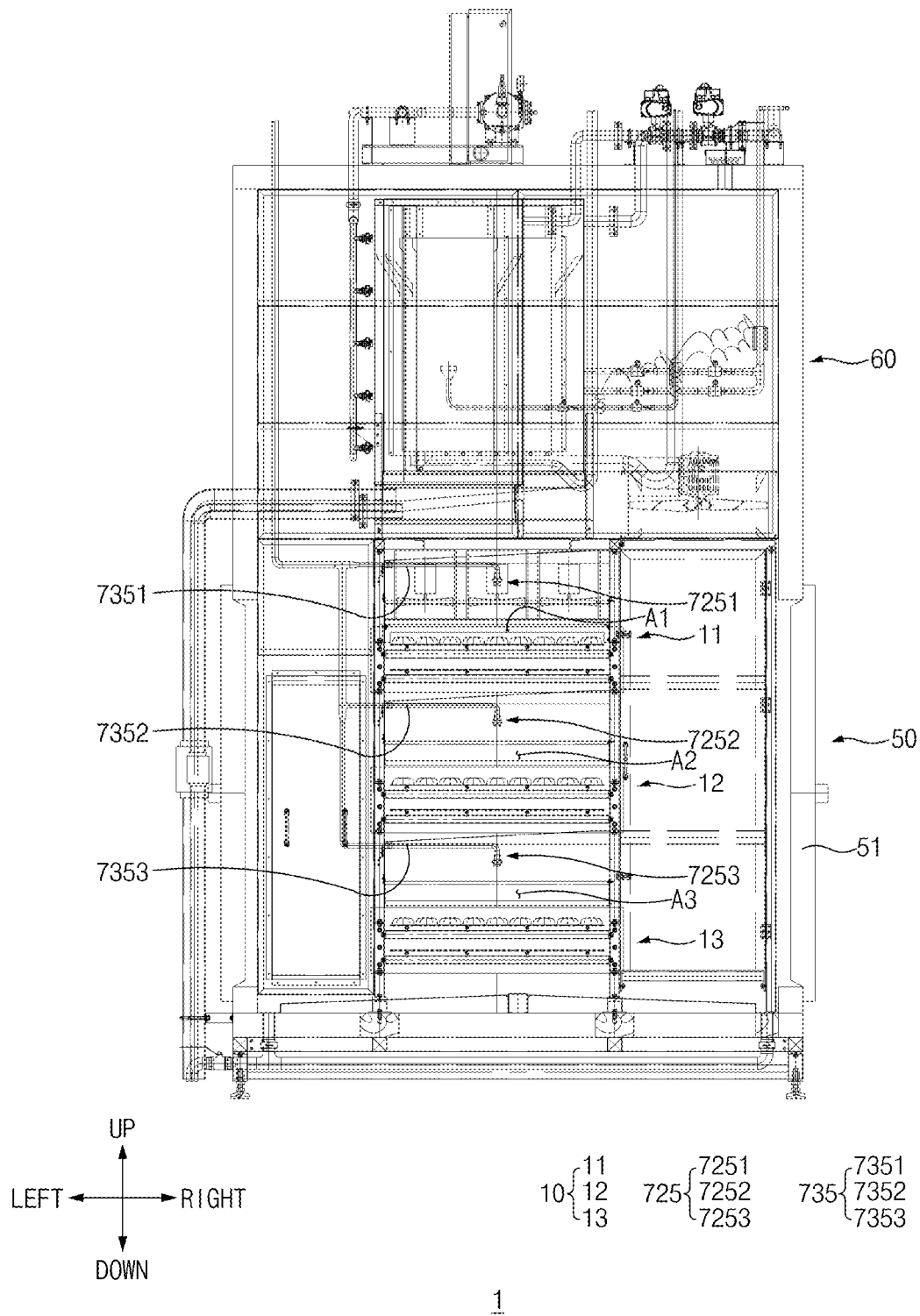
FIG. 4 is a view of a food processing system when viewed forward from a rear side so that an inner structure thereof is exposed according to an embodiment of the present invention.
Figure 5:
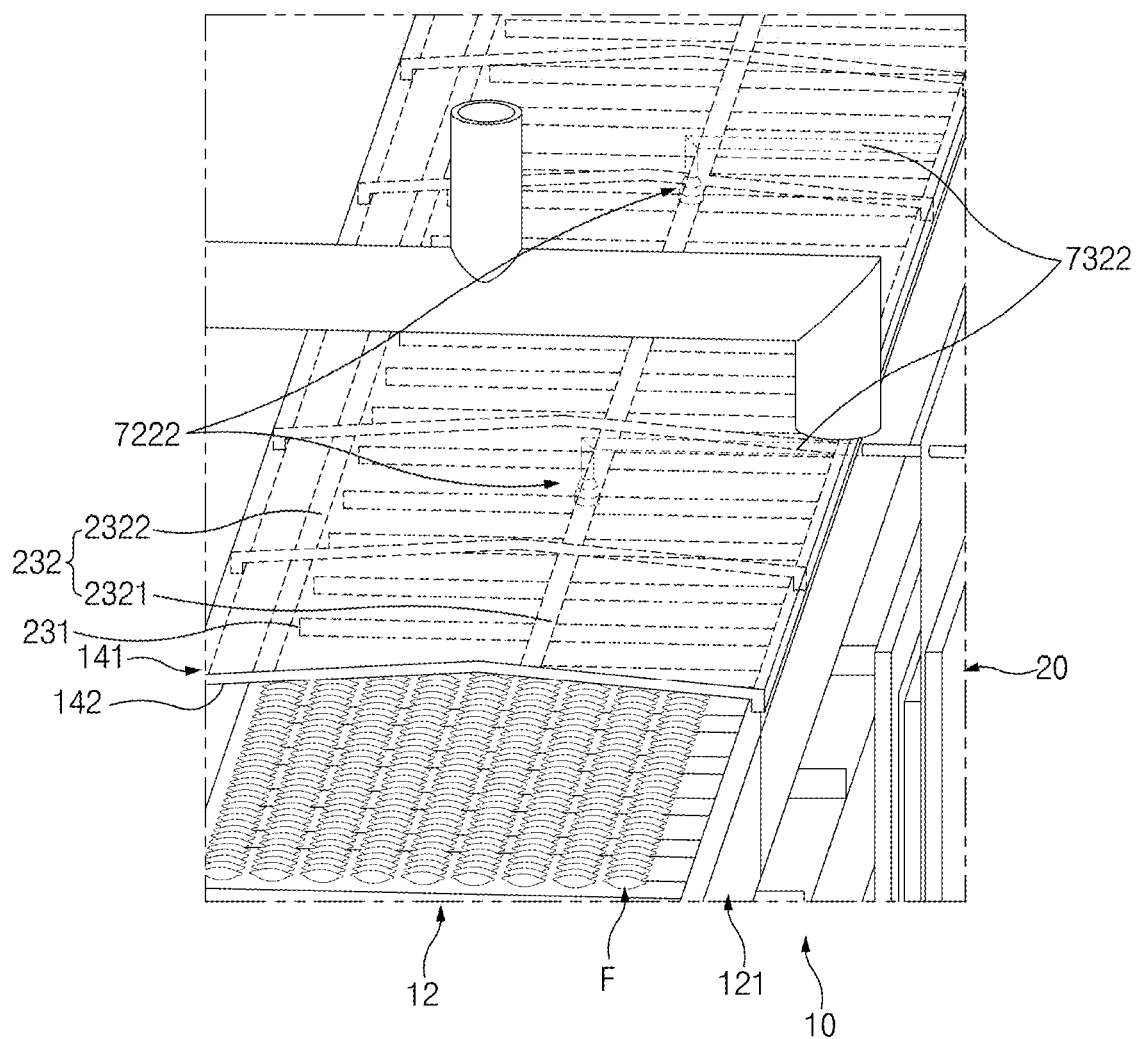
FIG. 5 is a view illustrating a portion of an inner structure of a steaming unit according to an embodiment of the present invention.

FIG. 1 is a perspective view of a food processing system 1 according to an embodiment of the present invention. FIG. 2 is a view of a food processing system according to an embodiment of the present invention when viewed downward from top to bottom in a state in which an inner structure of the food processing system is exposed according to an embodiment of the present invention. FIG. 3 is a view of a food processing system according to an embodiment of the present invention when viewed from a side in a state in which an inner structure of the food processing system is exposed according to an embodiment of the present invention. FIG. 4 is a view of a food processing system according to an embodiment of the present invention when viewed forward from a rear side to a front side so that an inner structure thereof is exposed according to an embodiment of the present invention. FIG. 5 is a view illustrating a portion of an inner structure of a steaming unit 20 according to an embodiment of the present invention.

The food processing system 1 according to an embodiment of the present invention includes a transport unit 10, processing units 20, 30, 40 and 50, and a cleaning unit 70. The food processing system 1 may further include a defrosting unit 60, a processor and an inverter. In this specification, front and rear, left and right, and upward and downward directions are relative directions used for convenience of explanation and may be changed according to a state in which the food processing system 1 is arranged.

Processing Units (20, 30, 40, 50)

Each of the processing units 20, 30, 40 and 50 is a portion through which the transport unit 10 passes and which defines an internal space in which foods F transported by the transport unit 10 are processed. The processing units 20, 30, 40 and 50 may include a steaming unit 20, a cooling unit 30, a pre-freezing unit 40, and a freezing unit 50. One of the steaming unit 20, the cooling unit 30, the pre-freezing unit 40, and the freezing unit 50 recited above may be referred to as a first processing unit, and the other may be referred to as a second processing unit. The chamber may include a steaming chamber 21 constituting the steaming unit 20, a cooling chamber 31 constituting the cooling unit 30, a pre-freezing chamber 41 constituting the pre-freezing unit 40, and a freezing chamber 51 constituting the freezing unit 50.

The internal space may include a first space A1, a second space A2, which does not overlap the first space A1 and is a space different from the first space A1, and a third space A3 which does not overlap each of the first space A1 and the second space A2. The internal space may be provided in three stages by including the first space A1, the second space A2, and the third space A3 that are disposed in this order downward. However, the number of stages is not limited thereto.

The steaming unit 20 is a portion provided to perform steam processing for cooking the foods F by using steam. The steaming unit 20 may perform the steam processing on the foods F transported by the transport unit 10. The steaming unit 20 may include the steaming chamber 21 for defining a steaming space therein, the steaming chamber 21 being a portion of the internal space, and include a steam providing means disposed inside the steaming chamber 21. The steam providing means may be provided in plurality. The steaming space may be divided into steaming division spaces.

The steaming chamber 21 may have a shape of a box that is opened in the front and rear direction. The transport unit 10 may pass through openings of the steaming chamber 21 in the front and rear direction. Thus, the foods F, which are transferred by the transport unit 10 in the rear direction, may be steamed while passing through the steaming space. For the effective steaming, a steaming gate capable of temporarily closing each of the openings of the steaming chamber 21 in the front and rear direction to seal or open the steaming space may be disposed in the opening in the front and rear direction.

The steam providing means may be disposed at a position corresponding to each of stages of the transport unit 10 having multiple stages and forcibly supply steam to each of the steaming division spaces. Thus, the steam providing means may include a steam generation means, which heats the water to generate the steam, and a steam discharging means which discharges the steam generated from the steam generation means to each of the steaming division spaces. The steam generation means may be a water heater, and the steam discharging means may be provided in a pipe type.

Among the plurality of steam providing means, the steam providing means disposed at the positions corresponding to different stages, respectively, may operate independently of each other. Thus, the temperature and discharge amount of the steam, which is discharged into the steaming division space corresponding to each of the transport stages, may be different according to situations. For such individual control, a steaming temperature sensor that obtains the temperature may be disposed in each of the steaming division spaces. The steam providing means corresponding to the steaming temperature sensor may be controlled according to the temperature obtained by the steaming temperature sensor.

The steam discharging means may be disposed below conveyors 111, 121 and 131 included in the transport stages 11, 12 and 13, respectively, and discharge the steam upwardly to steam the foods F seated and transferred on top surfaces of the conveyors 111, 121 and 131, respectively. The steam discharging means may include left-right pipes 231 and front-rear pipes 232, which receive the steam from the steam generation means and allow the steam to flow therein. The left-right pipes 231 may extend in the left and right direction, and the front-rear pipes 232 may extend in the front and rear direction.

The plurality of front-rear pipes 232 may be disposed at both ends and a center of each of the conveyors 111, 121 and 131 in the left and right direction, and the plurality of left-right pipes 231 may be disposed at predetermined intervals between the front-rear pipes 232 in the front and rear direction. Steam discharge holes or nozzles may be defined upwardly at predetermined intervals in the left-right pipe 231 and the front-rear pipe 232 in the left and right direction and the front and rear direction, respectively, and discharge the steam upwardly. Here, the nozzles are different from nozzles 722, 723, 724 and 725 included in the cleaning unit 70. Due to such arrangement of the front-rear pipes 232 and the left-right pipes 231, the foods F in the steaming space may be uniformly steamed by the injected steam. The temperature in the steaming unit 20 may be 95° C. to 99° C., and the foods F discharged from the steaming unit 20 may have a temperature of 75° C. to 85° C., preferably 80° C.

The left-right pipes 231 may be communicated with a central front-rear pipe 2321 of the front-rear pipes 232, which is disposed at the center. Thus, the central front-rear pipe 2321 may provide each of the left-right pipes 231 with the steam. The front-rear pipe 232 may include the central front-rear pipe 2321, and an outer front-rear pipe 2322 disposed at each of left and right sides of the central front-rear pipe 2321. The outer front-rear pipe 2322 may be disposed at a center of the conveyor 111, 121 or 131 in the upward and downward direction and at each of both sides of the conveyor 111, 121 or 131 in the left and right direction. The central front-rear pipe 2321 may be disposed at a lower side of the conveyor 111, 121 or 131 in the upward and downward direction and at a center of the conveyor 111, 121 or 131 in the left and right direction. That is, the central front-rear pipe 2321 may be disposed downward from the outer front-rear pipe 2322.

The steaming chamber 21 may have a dual structure. That is, the steaming chamber 21 may have a shape in which an outer steaming chamber surrounds an inner steaming chamber that defines a steaming space. Openings may be further defined in the steaming chamber 21 in the left and right direction. Dual steaming doors may be provided to open and close the openings in the left and right direction.

The cooling unit 30 is a component provided to perform cooling on the foods F transported from the steaming unit 20 by the transport unit 10. The cooling means a processing method of colling the foods F by exposing the foods F to outside air or allowing the outside air to flow around the foods F, without using a separate refrigerant or the like.

The cooling unit 30 may include the cooling chamber 31 for defining a cooling space therein, the cooling chamber 31 being a portion of the internal space, and the cooling chamber 31 may have an opening that is opened so that the outside air enters and exits the cooling space therethrough. The cooling unit 30 may include an outside air providing means 33 disposed inside the cooling chamber 31 to forcibly supply the outside air to the cooling space. The cooling unit 30 may include an outside air providing means 33 disposed inside the cooling chamber 31 to forcibly supply the outside air to the cooling space. The cooling unit 30 may be disposed behind the steaming unit 20.

The cooling space may be divided into cooling division spaces that include a first cooling division space, a second cooling division space, and a third cooling division space. The first space A1 may include the first cooling division space, the second space A2 may include the second cooling division space, and the third space A3 may include the third cooling division space.

The cooling chamber 31 may have a shape of a box that is opened in the front and rear direction. The transport unit 10 may pass through openings of the cooling chamber 31 in the front and rear direction. Thus, the foods F transferred by the transport unit 10 in the rear direction may be cooled while passing through the cooling space.

The pre-freezing unit 40 is a component provided to pre-freeze the foods F cooled and transported by the transport unit 10. The pre-freezing means a processing method of cooling the foods F by allowing air cooled using a refrigerant to flow around the foods F. The pre-freezing unit 40 may be disposed behind the cooling unit 30.

The pre-freezing unit 40 may include a pre-freezing chamber 41 for defining a pre-freezing space therein, the pre-freezing chamber 41 being a portion of the internal space. The pre-freezing chamber 41 may have a shape of a box that is opened in the front and rear direction. The transport unit 10 may pass through openings of the pre-freezing chamber 41 in the front and rear direction. Thus, the foods F transferred by the transport unit 10 in the rear direction may be pre-frozen while passing through the pre-freezing space.

The pre-freezing space may be divided into pre-freezing division spaces that include a first pre-freezing division space, a second pre-freezing division space, and a third pre-freezing division space. The first space A1 may include the first pre-freezing division space, the second space A2 may include the second pre-freezing division space, and the third space A3 may include the third pre-freezing division space.

The pre-freezing unit 40 may include a pre-freezing air providing means disposed in the pre-freezing chamber 41 to forcibly supply the air cooled with the refrigerant to the pre-freezing space. The pre-freezing unit 40 may include a pre-freezing air generation means capable of cooling the air through heat exchange between the refrigerant and the air and providing the pre-freezing air providing means with the cooled air. The pre-freezing air generation means 43 may be disposed above the pre-freezing chamber 41. The pre-freezing air generation means 43 may be a brine cooler using an indirect cooling method, using a refrigerant including salt water or the like.

The temperature in the pre-freezing unit 40 may be 3° C. to 7° C., preferably 5° C., and the foods F discharged from the pre-freezing unit 40 may have a temperature of 35° C. to 45° C., preferably 40° C.

The freezing unit 50 is a component provided to freeze the foods F pre-frozen and transported by the transport unit 10. The freezing unit 50 may be disposed behind the pre-freezing unit 40. The freezing unit 50 may include a freezing chamber 51 for defining a freezing space therein, the freezing chamber 51 being a portion of the internal space. The freezing chamber 51 may have a shape of a box that is opened in the front and rear direction. The transport unit 10 may pass through openings of the freezing chamber 51 in the front and rear direction. Thus, the foods F transferred by the transport unit 10 in the rear direction may be frozen while passing through the freezing space.

The freezing space may be divided into freezing division spaces that include a first freezing division space, a second freezing division space, and a third freezing division space. The first space A1 may include the first freezing division space, the second space A2 may include the second freezing division space, and the third space A3 may include the third freezing division space.

The freezing unit 50 may include a freezing module that provides cool air that is cooled air. That freezing module may include a freezing air providing means and a freezing air generation means. The freezing air providing means may be disposed inside the freezing chamber 51 to forcibly supply the air cooled with the refrigerant to the freezing space. The freezing air generation means may cool the air through heat exchange between the refrigerant and the air and provide the freezing air providing means with the cooled air. The freezing air generation means may be disposed above the freezing chamber 51. The freezing air generation means may be a freezing device using a refrigerant such as R-404 or R-507.

The temperature in the freezing unit 50 may be −37° C. to −40° C., and the foods F discharged from the freezing unit 50 may have a temperature of −5° C. to −10° C., preferably −7° C. The foods F transported by the transport unit 10 may be gradually cooled while passing through the cooling unit 30, the pre-freezing unit 40, and the freezing unit 50 in this order, thereby minimizing a sharp temperature change of the foods F and finally discharging the foods F in a frozen state. As the cooling is gradually performed, the load of the freezing unit 50 may be reduced.

At least one of the cooling unit 30, the pre-freezing unit 40, or the freezing unit 50 may include a plurality of air providing means, each of which is disposed at a position corresponding to each of the stages of the transport unit 10 and forcibly supplies the air. Such an air providing means may be the outside air providing means in the cooling unit 30, the pre-freezing air providing means in the pre-freezing unit 40, or the freezing air providing means in the freezing unit 50. The air providing means may suction and process the outside air to provide each of the chambers with the air, but may reprocess the air used in the chamber and provide the air back for the chamber.

Among the plurality of air providing means, the air providing means disposed at the positions corresponding to different stages, respectively, may operate independently of each other. Thus, the foods F seated on the transport stages may be processed at different temperatures, respectively. For such individual control, a temperature sensor that obtains the temperature may be disposed at a position adjacent to each of the transport stages. The air providing means corresponding to the temperature sensor may be controlled according to the temperature obtained by the temperature sensor.

At least one of the cooling unit 30, the pre-freezing unit 40, or the freezing unit 50 may include a damper for air volume control, which is provided to adjust a flow rate of the air provided for the plurality of air providing means. The damper for air volume control may have a pipe-shaped appearance and be disposed in the middle of a flow path through which the air flows. The damper may include a damper member, which is disposed inside the damper and of which a position is adjustable, and adjust the position of this damper member, thereby adjusting the air volume provided through the damper for air volume control.

Air curtains provided to spray air onto the foods F may be provided at an inlet and an outlet, respectively, of each of the cooling unit 30, the pre-freezing unit 40, and the freezing unit 50. As the air curtains are disposed, foreign matters present on the foods F transported by the transport unit 10 may be removed, and foreign matters other than the foods F may be blocked from being introduced into the cooling chamber 31, the pre-freezing chamber 41, and the freezing chamber 51.

The pre-freezing unit 40 and the cooling unit 30 cool the foods F but do not freeze the foods F and thus, may constitute a cooler. That is, the cooler is a portion that is disposed between the freezing unit 50 and the steaming unit 20 and provided to cool the foods F, which are steamed and transported by the transport unit 101, before the foods F are transferred to the freezing unit 50.

The cooling unit 30, the pre-freezing unit 40, and the freezing unit 50 may have different lengths in the front and rear direction. The lengths of the cooling unit 30, the pre-freezing unit 40 and the freezing unit 50 in the front and rear direction may be longer in the reverse order mentioned.

The food processing system 1 according to an embodiment of the present invention may further include the defrosting unit 60. The defrosting unit 60 is a component that is connected to the freezing unit 50 so as to remove frost formed inside the freezing unit 50. The defrosting unit 60 may be provided to inject the air into the freezing unit 50 and remove the frost. The defrosting unit 60 may inject the air into the freezing module, not into the freezing chamber 51, and remove the frost occurring in the freezing module.

The defrosting unit 60 may include a plurality of defrosting nozzles, an air tank, and an air drying module. The defrosting nozzles may be connected to the freezing module and provided to inject air into the freezing air generation means of the freezing module. The air tank may deliver the dried air stored therein to the defrosting nozzles through pipes. A valve may be disposed in each of the pipes and adjust an amount of the air delivered to each of the defrosting nozzles. The air drying module may be connected to the air tank, and suction and dry the air inflowing from the outside so that the air is stored in the air tank. The air drying module may be a dehumidifier that performs dehumidification in such a manner that air is cooled to condense steam, or performs dehumidification using an absorbent such as silica gel. However, the type of the air drying module is not limited thereto.

The defrosting nozzle may be disposed to face a portion of the freezing air generation means, which is prone to the frost. The defrosting nozzles may be disposed in a grid shape to face the frozen air generation means at a side surface of the frozen air generation means and inject high-pressure air to physically remove the frost.

Transport Unit (10)

The transport unit 10 is a component provided to continuously transport foods F. The transport unit 10 may be provided in multiple stages. The stages of the transport unit 10 may be disposed to be spaced apart from each other vertically. As in an embodiment of the present invention, the transport unit 10 may be provided in three stages by including a first transport stage 11, a second transport stage 12, and a third transport stage 13 that are disposed in this order downward. However, the number of stages is not limited thereto.

A space in a housing of the processing units 20, 30, 40 and 50 may be divided into a first space A1, a second space A2, and a third space A3, but the number of spaces divided is not limited thereto. The first transport stage 11 may be disposed in the first space A1, the second transport stage 12 in the second space A2, and the third transport stage 13 in the third space A3.

The first space A1, the second space A2, and the third space A3 may be separated vertically based on lower ends of the conveyors 111, 121 and 131, respectively. When explained based on the steaming space, a space of the first space A1, which is inside the steaming unit 20, may be a first steaming division space, a space of the second space A2, which is in the steaming unit 20, may be a second steaming division space, and a space of the third space A3, which is in the steaming unit 20, may be a third steaming division space. A space between the lower ends of adjacent conveyors of the conveyors 111, 121 and 131 may be the division space.

A food F supply equipment may be disposed in front of the transport unit 10. The food F supply equipment may be disposed parallel to each of the stages of the transport unit 10. Alternatively, the food F supply equipment may be disposed at a side in a left and right direction of each of the stages of the transport unit 10 and transfer the foods F to the transport unit 10 in the left and right direction, or the food F supply equipment may be a rotary supply equipment having a rotating structure, but not transfer the foods F to the transport unit 10 through a path formed by a straight line. The type of the food F supply equipment is not limited thereto.

The stages of the transport unit 10 may include the conveyors 111, 121 and 131, respectively, which are provided to transport the foods F. The transport stages may include a first conveyor 111, a second conveyor 121 and a third conveyor 131, respectively. Each of the conveyors 111, 121 and 131 may extend in the front and rear direction and be provided so that a plurality of foods F may be arranged in the left and right direction and the front and rear direction. Each of the conveyors 111, 121 and 131 may include a plurality of rollers and a belt wound on an outer circumference of each of the plurality of rollers and allow the belt to rotate by rotation of the rollers so that the foods F disposed on a top surface of the belt may be transported in a predetermined direction. In an embodiment of the present invention, as the rollers rotate in an axial direction that is the left and right direction perpendicularly crossing the front and rear direction, the belt may transfer the foods F in a rear direction.

In order to drive the conveyors 111, 121 and 131, the transport unit 10 may further include a driving module including a motor, which generates a rotational driving force and transmits the rotational driving force to the rollers, and so on. A single conveyor 111, 121 or 131 may be disposed over the entirety of the food processing system 1 in the front and rear direction. Alternatively, the conveyor 111, 121 or 131 may be divided into conveyor units per a predetermined section, and a plurality of continuous conveyor units may constitute the conveyor 111, 121 or 131. When the conveyor 111, 121 or 131 includes the plurality of conveyor units, different driving modules may be disposed in the conveyor units and drive the conveyor units, respectively.

Each of the stages of the transport unit 10 may further include a transport cover 141 that covers the conveyor 111, 121 or 131 at upper side of the conveyor 111, 121 or 131 passing through the interior of the steaming unit 20 included in the processing units 20, 30, 40 and 50. As the transport cover 141 covers the conveyor 111, 121 or 131, a steaming separation space in which the conveyor 111, 121 or 131 is disposed between a lower side of the transport cover 141 and a steam pipe may be defined in each of the stages, and the first steaming separation space, the second steaming separation space, and the third steaming separation space, which are steaming separation spaces of the stages, respectively, may be separated from each other. The first transport stage 11 may define the first steaming separation space even without including the transport cover 141 because another transport stage to be disposed on the conveyor 111 is absent. The transport cover 141 of the second transport stage 12 may separate the conveyor 121 of the second transport stage 12 from the first transport stage 11 and define the second steaming separation space. The transport cover of the third transport stage 13 may separate the conveyor 131 of the third transport stage 13 from the second transport stage 12 and define the third steaming separation space.

The transport cover 141 may have a shape that is upwardly inclined toward the inside based on the left and right direction. Thus, the transport cover 141 may have a shape in which a distance from the conveyor 111, 121 or 131 to the transport cover 141 gradually increases toward a center. As the transport cover 141 has such a shape, water may be guided to drop to the outside in the left and right direction even when the water is formed at a bottom surface of the transport cover 141 due to steam. Accordingly, the water may be prevented from dropping to the foods F disposed at the center in the left and right direction.

Each of the stages of the transport unit 10 may further include a baffle plate 142 protruding from the bottom surface of the transport cover 141 toward the conveyor 111, 121 or 131. The baffle plate 142 may extend in the left and right direction and be provided in plurality to be disposed to be spaced apart from each other in the front and rear direction. Similarly to the transport cover 141 when viewed in the front and rear direction, the baffle plate 142 may have a shape that is upwardly inclined toward the inside based on the left and right direction, and have a predetermined thickness in the upward and downward direction. The baffle plate 142 may further divide each of the steaming separation spaces, which are separated vertically from each other, in the front and rear direction.

The baffle plate 142 may accommodate a thermal insulation material therein. The thermal insulation material may be glass wool, but the type thereof is not limited thereto. As the baffle plate 142 accommodates the thermal insulation material, the steaming separation spaces may be effectively thermally insulated from each other.

Processor

The processor is a component, which executes a control command and includes a device capable of executing logical operation, and may include a central processing unit (CPU), etc. The processor may be connected to various components and deliver a signal in response to the control command to each of the components to execute control, and may be connected to various sensors or acquisition parts and receive acquired information in the forms of a signal. Thus, in an embodiment of the present invention, the processor may be electrically connected to various components included in the food processing system 1. As the processor may be electrically connected to various components, the processor may communicate with the components by being connected to the components by a conductive line or by further including a communication module capable of performing wireless communication.

The food processing system 1 may further include a storage medium, and control commands executed by the processor may be stored and utilized in the storage medium. The storage medium may be a device such as a hard disk drive (HDD), a solid state drive (SSD), a server, a volatile medium, or a non-volatile medium, but the type thereof is not limited thereto. In addition, data, etc., which are necessary for the processor to accomplish operations may be further stored in the storage medium.

Cleaning Unit (70)

Figure 6:
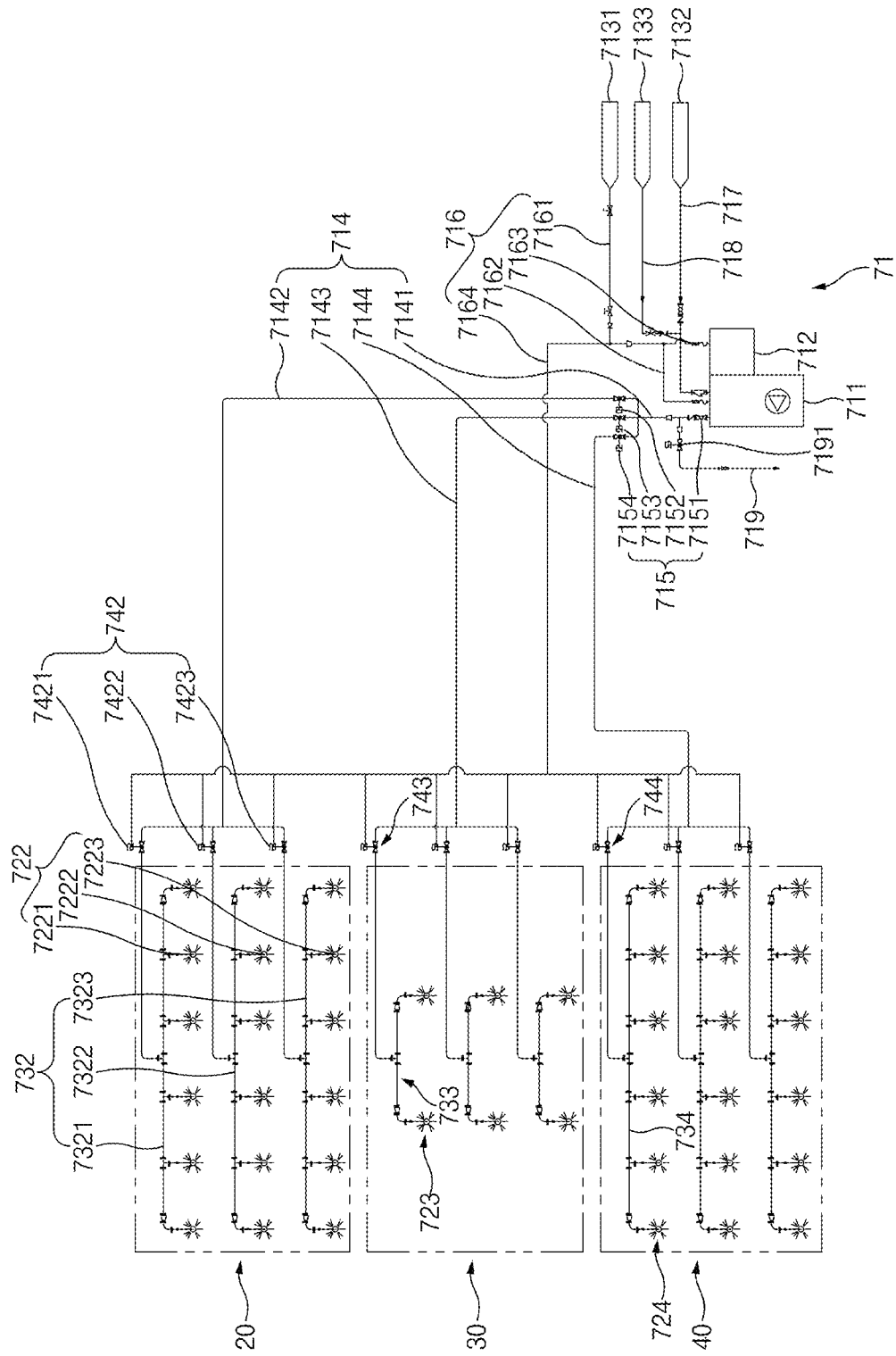
FIG. 6 is a conceptual view of a cleaning unit included in a food processing system according to an embodiment of the present invention.

FIG. 6 is a conceptual view of the cleaning unit 70 included in the food processing system 1 according to an embodiment of the present invention. The conceptual view in FIG. 6 does not illustrate the freezing nozzle 725 disposed in the freezing unit 50. The freezing nozzle 725 may be identified in FIG. 4.

The cleaning unit 70 includes the nozzles 722, 723, 724 and 725 and a liquid supply module 71 in order to clean the interior of processing units 20, 30, 40 and 50. As the cleaning unit 70 is used, cleaning of the internal space may be carried out only by control without the need for the worker to enter the processing units herself or himself and thus, cleaning-in-place of the processing units 20, 30, 40 and 50 is possible. As the cleaning-in-place is possible, time required for the cleaning of the food processing system 1 is reduced and the worker's risk of injuries is reduced.

The nozzles 722, 723, 724 and 725 inject liquid, which is any one of a cleaning material and cleaning water, into the internal space in order to clean a chamber interior of each of the processing units 20, 30, 40 and 50, and may be provided in plurality. The liquid supply module 71 supplies selectively any one of the cleaning material and the cleaning water to the plurality of nozzles 722, 723, 724 and 725 so that the foregoing selective liquid injection is carried out. The food processing system 1 may further include an inverter provided to adjust pressure at which a pump 711 forcibly supplies the liquid. The inverter may be electrically connected to the pump 711 and control the pump 711 linearly. The inverter may be electrically connected to the processor.

The cleaning unit 70 may further include a control valve box 712 that controls the pump 711. The control valve box 712 includes valves for controlling an operation of the pump 711 and the liquid supplied to the pump 711, and controls such valves with a pneumatic device that uses compressed air received from a compressed air supply terminal 7131 through a compressed air control pipe 7163.

The cleaning material supplied by the liquid supply module 71 may be at least one of steam, cleaning foam, sanitizer or compressed air. The cleaning foam and the sanitizer may be supplied through a cleaning material supply terminal to the pump 711 included in the liquid supply module 71, and the compressed air may be introduced from the compressed air supply terminal 7131 into a compressed air supply pipe 7161, which is included in a compressed air pipe 716, and then supplied to the pump 711 through a compressed air delivery pipe 7162. The cleaning foam, the sanitizer and the compressed air may be forcibly supplied to the nozzles 722, 723, 724 and 725 through a liquid transfer pipe 714 by the pump 711. A cleaning water supply terminal may be connected to the pump 711 so that the cleaning water is delivered to the pump 711 and then forcibly supplied to the nozzles 722, 723, 724 and 725 through the liquid transfer pipe 714.

A hot water supply terminal 7132, which supplies hot water that is water having a higher temperature than general water, to the pump 711 through a hot water pipe 717, and a water supply terminal 7133 which supplies water to the pump 711 through a water pipe 718 may be further disposed. The water pipe 718 may be connected to the hot water pipe 717 so that the supply of the liquid to the pump 711 is not discontinued to ensure that an automatic CIP operation is not interrupted. The cleaning water may include the hot water and the water. The hot water may be water obtained by heating the water.

The plurality of nozzles 722, 723, 724 and 725 may be disposed in the processing units 20, 30, 40 and 50, respectively. The nozzles 722, 723, 724 and 725 disposed in the steaming unit 20 may be steaming nozzles 722, the nozzles 722, 723, 724 and 725 disposed in the cooling unit 30 may be cooling nozzles 723, the nozzles 722, 723, 724 and 725 disposed in the pre-freezing unit 40 may be pre-freezing nozzles 724, and the nozzles 722, 723, 724 and 725 disposed in the freezing unit 50 may be freezing nozzles 725. The nozzles 722, 723, 724 and 725 disposed in the different processing units 20, 30, 40 and 50 may be controlled independently of each other. For example, a flow rate of the liquid injected through a nozzle of the plurality of nozzles 722, 723, 724 and 725, which is disposed in the first processing unit, and a flow rate of the liquid injected through a nozzle of the plurality of nozzles 722, 723, 724 and 725, which is disposed in the second processing unit, may be controlled to be independent of each other.

The plurality of nozzles 722, 723, 724 and 725 may include a plurality of first nozzles disposed in the first space A1, a plurality of second nozzles disposed in the second space A2, and a plurality of third nozzles disposed in the third space A3. When explained based on the steaming nozzles 722, the steaming nozzles 722 may include a first steaming nozzle 7221, which is the first nozzle disposed in the first steaming separation space, a second steaming nozzle 7222, which is the second nozzle disposed in the second steaming separation space, and a third steaming nozzle 7223 which is the third nozzle disposed in the third steaming separation space. Thus, each of the stages 11, 12 and 13, the left and right pipes 231, the front and rear pipes 232, and an inner surface of the transport cover 141 may be cleaned with the cleaning water, etc., that is injected from the steaming nozzles 722.

Each of the cooling nozzles 723, the pre-freezing nozzles 724, and the freezing nozzles 725 may include the nozzles 722, 723, 724 and 725 disposed in each of the spaces. The nozzles 722, 723, 724 and 725 disposed in the different spaces may be controlled independently of each other. Each of the nozzles 722, 723, 724 and 725 may be disposed to face downward in an upper region of each of the spaces. In addition, the nozzles 722, 723, 724 and 725 may be disposed to be spaced apart from each other in the front and rear direction and the upward and downward direction.

The liquid supply module 71 may include the liquid transfer pipe 714 that delivers the liquid from the pump 711 to the nozzles 722, 723, 724 and 725 disposed in the processing units 20, 30, 40 and 50, respectively. The liquid transfer pipe 714 may include a main transfer pipe 7141, which receives the liquid discharged from the pump 711, a steaming transfer pipe 7142, which is connected to the main transfer pipe 7141 and delivers the liquid to the steaming nozzles 722, a cooling transfer pipe 7143, which is connected to the main transfer pipe 7141 and delivers the liquid to the cooling nozzles 723, a pre-freezing transfer pipe 7144, which is connected to the main transfer pipe 7141 and delivers the liquid to the pre-freezing nozzles 724, and a freezing transfer pipe which is connected to the main transfer pipe 7141 and delivers the liquid to the freezing nozzles 725.

The liquid delivered through each of the liquid transfer pipes 714 may be distributed to the nozzles 722, 723, 724 and 725 through liquid distribution pipes 732, 733, 734 and 735 disposed in the processing units 20, 30, 40 and 50, respectively. That is, the nozzles 722, 723, 724 and 725 may be connected to the liquid transfer pipe 714 by using the liquid distribution pipes 732, 733, 734 and 735 as media, respectively. The liquid distribution pipes 732, 733, 734 and 735 may include a steaming distribution pipe 732, which delivers the liquid from the steaming transfer pipe 7142 to the steaming nozzles 724, a cooling distribution pipe 733, which delivers the liquid from the cooling transfer pipe 7143 to the cooling nozzles 723, a pre-freezing distribution pipe 734, which delivers the liquid from the pre-freezing transfer pipe 7144 to the pre-freezing nozzles 724, and a freezing distribution pipe 735 which delivers the liquid from the freezing transfer pipe to the freezing nozzles 725.

Each of the liquid distribution pipes 732, 733, 734 and 735 may include separate pipes disposed in the first space A1, the second space A2, and the third space A3, respectively. That is, when explained based on the steaming distribution pipe 732, the steaming distribution pipe 732 may include a first steaming distribution pipe 7321 connected to the first steaming nozzle 7221, a second steaming distribution pipe 7322 connected to the second steaming nozzle 7222, and a third steaming distribution pipe 7323 connected to the third steaming nozzle 7223. Each of the cooling nozzle 723, the pre-freezing nozzle 724, and the freezing nozzle 725 may have the liquid distribution pipes 732, 733, 734 and 735 connected to the nozzle 722, 723, 724 and 725 disposed in the spaces, respectively.

Referring to FIG. 4, it may be confirmed that a first freezing distribution pipe 7351 is connected to a first freezing nozzle 7251 disposed on the first transport stage 11 in the first freezing separation space, a second freezing distribution pipe 7352 is connected to a second freezing nozzle 7252 disposed on the second transport stage 12 in the second freezing separation space, and a third freezing distribution pipe 7353 is connected to a third freezing nozzle 7253 disposed on the third transport stage 13 in the third freezing separation space. In FIG. 5, the second steaming nozzle 7222 and the second steaming distribution pipe 7322, which are disposed between an upper side of the second transport stage 12 and a lower side of the transport cover 141 in the steaming part 20, may be confirmed.

A distribution valve 742, 743 or 744 that adjusts opening or closing of the liquid distribution pipe 732, 733, 734 or 735 may be disposed in the liquid distribution pipe 732, 733, 734 or 735 so that the liquid is supplied or not supplied from the liquid transfer pipe 714 to the liquid distribution pipe 732, 733, 734 or 735. That is, a steaming distribution valve 742 may be disposed in the steaming distribution pipe 732, a cooling distribution valve 743 in the cooling distribution pipe 733, a pre-freezing distribution valve 744 in the pre-freezing distribution pipe 734, and a freezing distribution valve in the freezing distribution pipe 735 so as to adjust the opening or closing of each of the liquid distribution pipes 732, 733, 734 and 735. When explained based on the steaming distribution pipe 732, a first steaming distribution valve 7421 may be disposed in the first steaming distribution pipe 7321, a second steaming distribution valve 7422 in the second steaming distribution pipe 7322, and a third steaming distribution valve 7423 in the third steaming distribution pipe 7323.

The distribution valves 742, 743 and 744 may be pneumatic valves. A working air pipe 7164 may be connected to each of the distribution valves 742, 743 and 744 so that as the compressed air is supplied, the opening or closing of each of the distribution valves 742, 743 and 744 is controlled.

A transfer valve 715 that adjusts opening or closing of each of liquid transfer pipes 714 may be disposed in the liquid transfer pipe 714 so that the liquid is supplied or not supplied through the liquid transfer pipe 714. That is, a steaming transfer valve 7152 may be disposed in the steaming transfer pipe 7142, a cooling transfer valve 7153 in the cooling transfer pipe 7143, a pre-freezing transfer valve 7154 in the pre-freezing transfer pipe 7144, a freezing transfer valve 715 in the freezing transfer pipe, and a main transfer valve 7151 in the main transfer pipe 7141 so as to adjust the opening or closing of each of the liquid transfer pipes 714.

A discharge pipe 719 may be connected to the pump 711 so that the liquid is discharged from the pump 711 to the outside. A discharge valve 7191 may be disposed in the discharge pipe 719 so as to control opening or closing of the discharge pipe 719. An injection valve may be connected to the pump 711 to serve as a passage through which cleaning materials such as cleaning foam and the sanitizer, are input from the outside. When a cleaning material tank is adjacent to the pump 711, one end may be connected to the cleaning material tank and the other end may be connected to the injection valve. Accordingly, the cleaning materials may be delivered to the pump 711.

The cleaning unit 70 may be controlled so that flow rates of the liquid injected by the nozzles 722, 723, 724 and 725 of the plurality of nozzles 722, 723, 724 and 725, which are connected to different liquid distribution pipes 732, 733, 734 and 735, are independent of each other. For example, each of the vales, etc., may be controlled so that a flow rate of the liquid injected by multiple first nozzles of the plurality of nozzles 722, 723, 724 and 725 and a flow rate of the liquid injected by another multiple second nozzles of the plurality of nozzles 722, 723, 724 and 725 are independent of each other. For another example, while the cleaning water is injected from the steaming nozzle 722 at a predetermined flow rate, the cleaning water may be injected from the pre-freezing nozzle 724 at a flow rate different from the predetermined flow rate.

In a working mode, the food processing system 1 may be controlled so that each of the processing units 20, 30, 40 and 50 operates for this purpose. A cleaning mode may be performed after the working mode is finished. The liquid supply module 71 may supply the compressed air to the freezing nozzle 725 after the cleaning mode is performed and finished, and remove moisture caused by the cleaning water or the like, which remains in the freezing unit 50.

Figure 7:
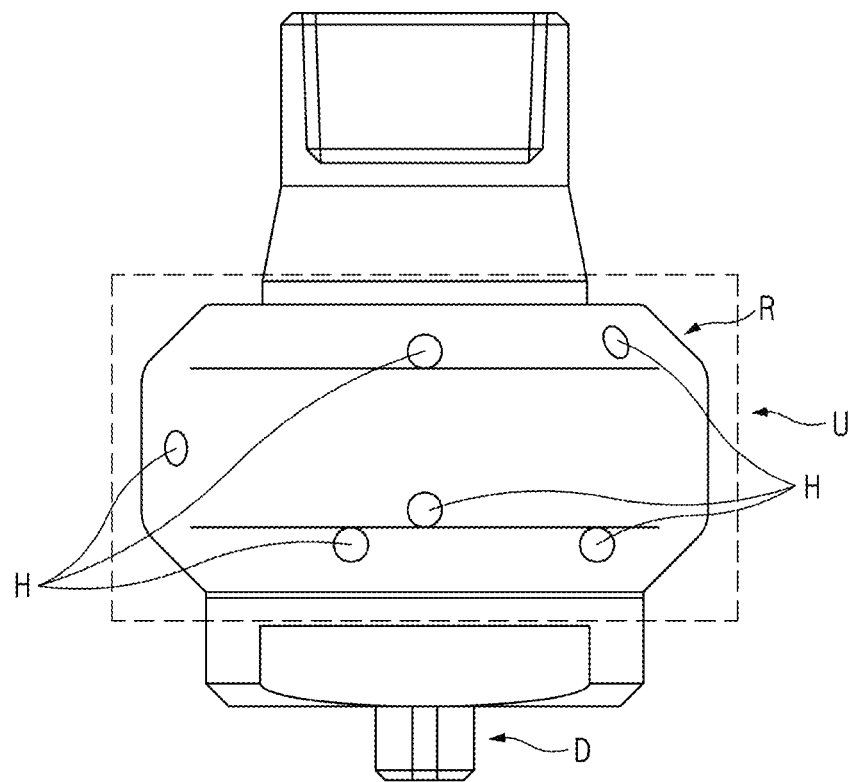
FIG. 7 is a view illustrating a nozzle of a food processing system according to an embodiment of the present invention.
Figure 8:
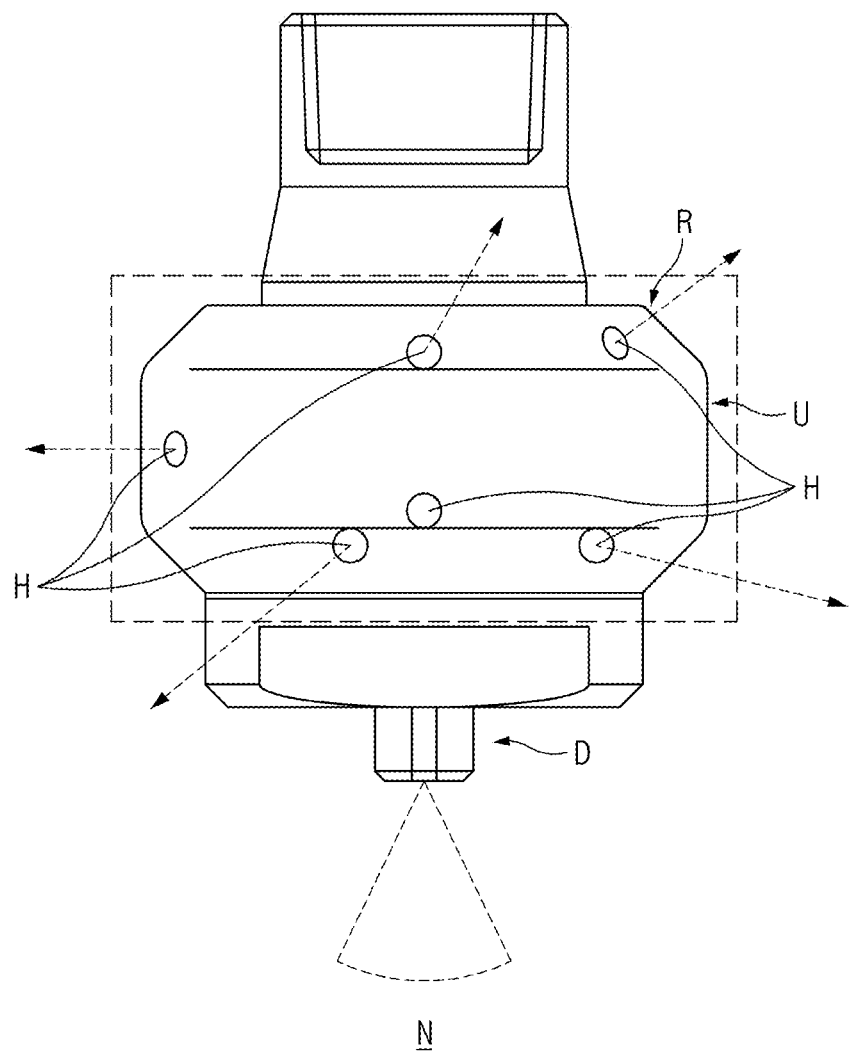
FIG. 8 is a view illustrating a shape in which liquid is injected by a nozzle of a food processing system according to an embodiment of the present invention.

FIG. 7 is a view illustrating a nozzle N of a food processing system 1 according to an embodiment of the present invention. FIG. 8 is a view illustrating a shape in which liquid is injected by the nozzle N of the food processing system 1 according to an embodiment of the present invention.

The nozzle N in FIGS. 7 and 8 is the same as each of the nozzles 722, 723, 724 and 725 in FIGS. 1 to 6. The nozzle N may include an upper injector U and a lower injector D, and may be divided into the lower injector D and the upper injector U. The upper injector U is a portion that is connected to each of liquid distribution pipes 732, 733, 734 and 735, and the lower injector D is a portion that is connected to a lower end of the upper injector U. The lower injector D may be provided to inject the liquid at pressure higher than pressure at which the upper injector U injects the liquid.

The lower injector D faces downward and is provided so that the liquid is injected downwardly while drawing a conical line. The upper injector U is provided to inject the liquid therearound above the lower injector D. Thus, a plurality of lower injection holes, which are defined in a direction that is downwardly inclined toward the outside, or a lower injection hole having a conical shape, in which a cross-sectional area taken along a plane perpendicularly crossing the upward and downward direction gradually increases downward, may be defined in the lower injector D so that the liquid is injected downwardly while drawing a conical line. A plurality of upper injection holes H, through which the liquid is injected in a direction crossing the upward and downward direction, may be defined in a rotary injector R, which is in a rectangle shown by dotted lines in the drawings and is a portion of the upper injector U. Directions in which the liquid is injected through the plurality of upper injection holes H, respectively, may be different from each other. For example, the plurality of upper injection holes H may be provided in two at each of an upper portion and a lower portion of the rotary injector R, and the liquid injection directions may have different angles with respect to a horizontal direction. Four of the plurality of upper injection holes H may be defined in a middle portion of the rotary injector R, and the liquid injection directions may have different angles with respect to the horizontal direction.

The rotary injector R may be provided to inject the liquid therearound while rotating. That is, a portion corresponding to the rotary injector R may be defined to be rotatable or may be rotatably coupled to each of the liquid distribution pipes 732, 733, 734 and 735. When the rotary injector R rotates, the other portion of the nozzle N may not rotate. As the nozzle N injects the liquid in such a method, the liquid may be injected uniformly into the internal space and a blind spot that is not injected may be reduced.

Figure 9:
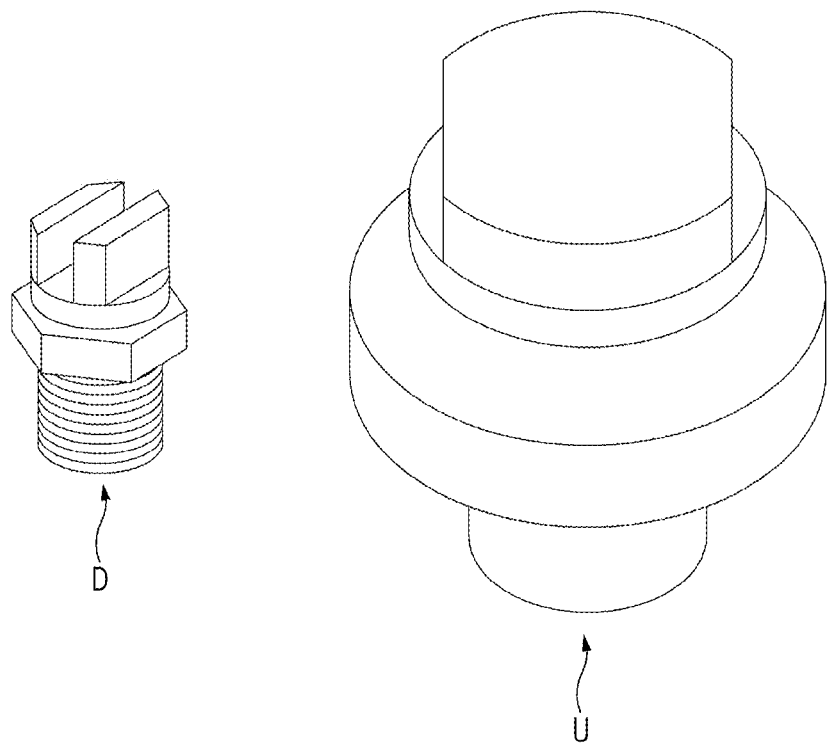
FIG. 9 is a view illustrating a nozzle of a food processing system, which is separated into a lower injector and an upper injector according to an embodiment of the present invention.
Figure 10:
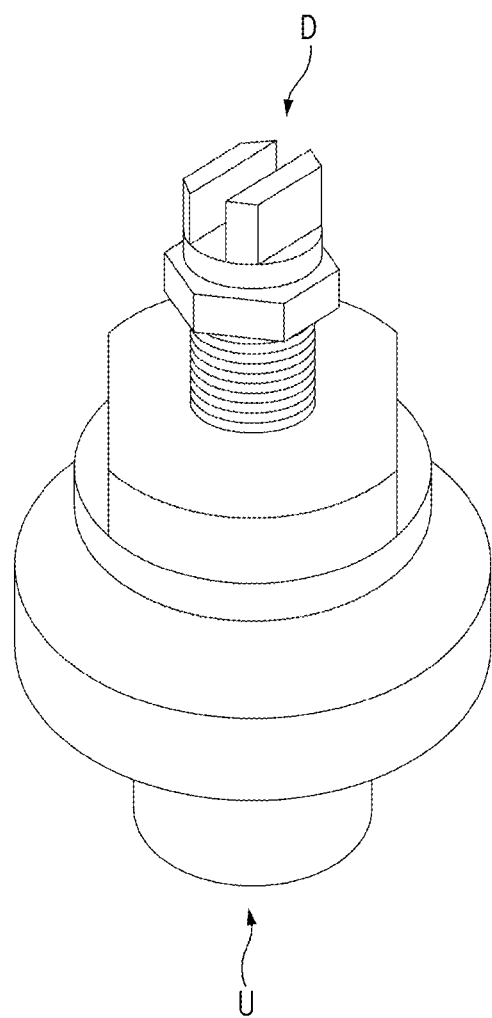
FIG. 10 is a view illustrating a state in which a lower injector is coupled to an upper injector in a food processing system according to an embodiment of the present invention.

FIG. 9 is a view illustrating a nozzle N of a food processing system 1, which is separated into a lower injector D and an upper injector U according to an embodiment of the present invention. FIG. 10 is a view illustrating a state in which the lower injector D is coupled to the upper injector U in the food processing system 1 according to an embodiment of the present invention.

The lower injector D may have an upper portion that is provided in a screw shape and coupled to a lower end of the upper injector U. As the lower injector D and the upper injector U are coupled to each other along a thread, replacement and maintenance of each of the parts of the nozzle N may be easily performed.

Figure 11:
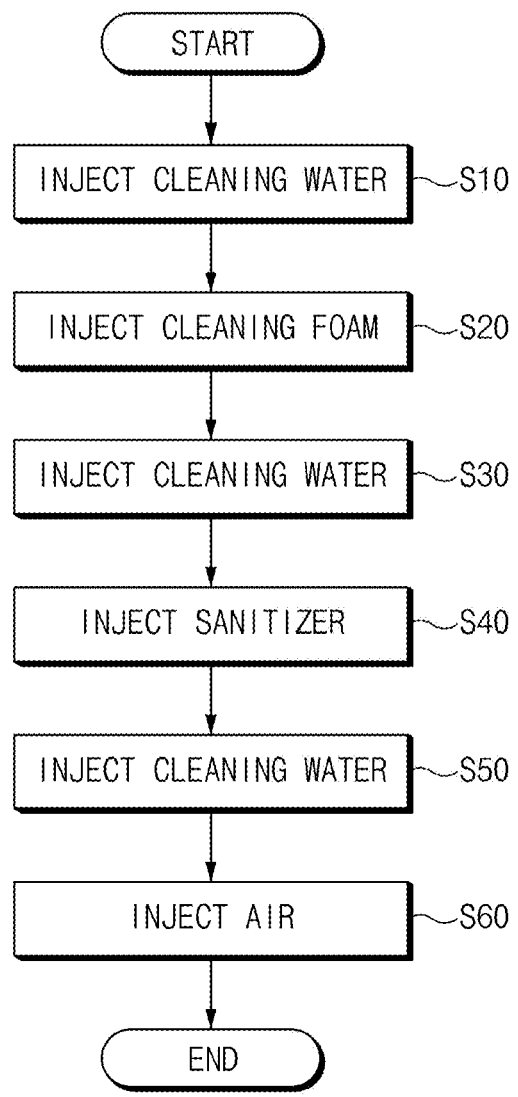
FIG. 11 is a flowchart of a method for cleaning a food processing system according to an embodiment of the present invention.

FIG. 11 is a flowchart of a method for cleaning a food processing system 1 according to an embodiment of the present invention.

In a cleaning mode, a liquid supply module 71 may supply liquid in order of cleaning water, cleaning foam, cleaning water, sanitizer, and cleaning water, to a plurality of nozzles 722, 723, 724 and 725. Specifically, when the cleaning mode starts, the cleaning water may be injected into an internal space by using the nozzles 722, 723, 724 and 725 for removal of residues present in the internal space (S10). The cleaning foam may be injected into the internal space by using the nozzles 722, 723, 724 and 725 after the residues are removed through the injecting of the cleaning water (S20). The cleaning water may be injected into the internal space by using the nozzles 722, 723, 724 and 725 for removal of the cleaning foam (S30). Thereafter, the sanitizer may be injected into the internal space by using the nozzles 722, 723, 724 and 725 (S40). The cleaning water may be injected into the internal space by using the nozzles 722, 723, 724 and 725 for removal of the sanitizer (S50). Such a cleaning mode is finished and then, if necessary, compressed air may be injected into a freezing unit 50 by using the nozzles 722, 723, 724 and 725 so as to remove moisture (S60).

Figure 12:
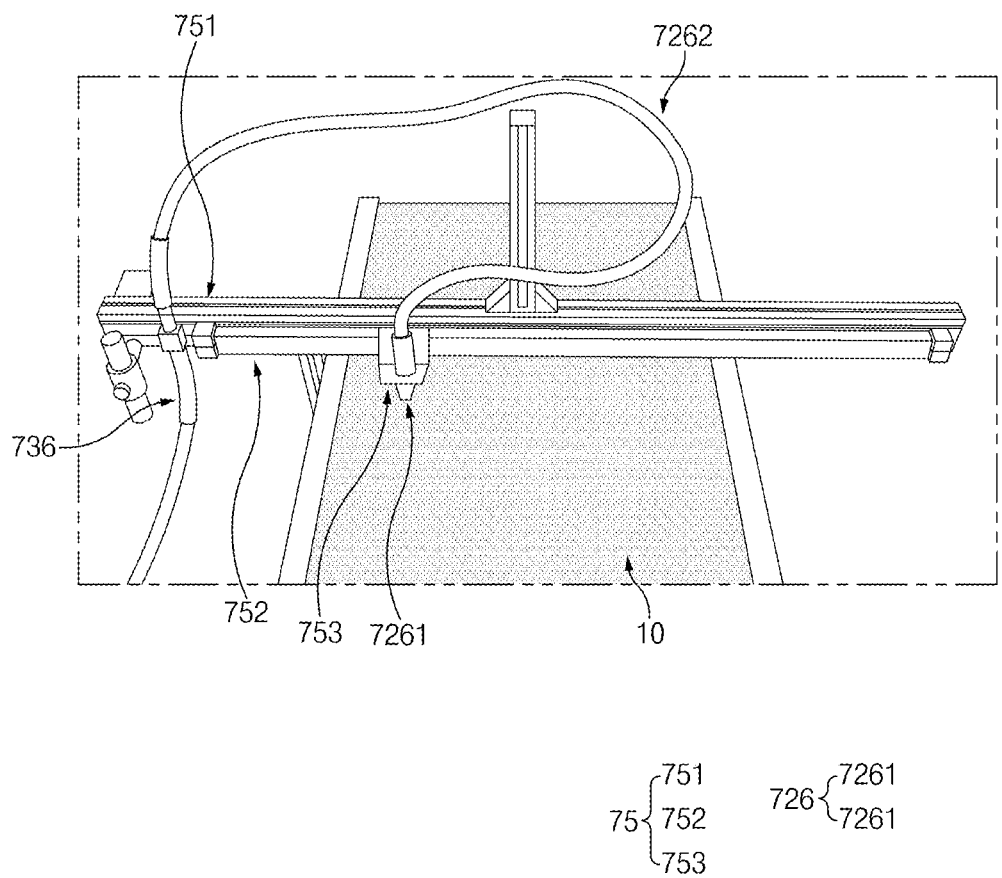
FIG. 12 is a view illustrating a nozzle arrangement state of a food processing system according to another embodiment of the present invention.

FIG. 12 is a view illustrating a nozzle arrangement state of a food processing system according to another embodiment of the present invention. The food processing system according to another embodiment of the present invention is similar to but partially different from the food processing system according to an embodiment of the present invention. Thus, the description of an embodiment of the present invention applies to another embodiment of the present invention, and only different matters are described below.

Referring to the drawing, a nozzle 7261, which receives liquid from a liquid supply module 71 and injects the liquid, may be disposed to be movable in the food processing system according to another embodiment of the present invention. Here, the liquid injected by the nozzle 7261 may be any one of cleaning material and cleaning water as in an embodiment of the present invention, and the types of the cleaning material and the cleaning water are also the same as those described in an embodiment.

A cleaning unit 70 according to another embodiment may include a nozzle part 726 that is connected to a liquid distribution pipe 736 and receives the liquid from the liquid supply module 71. The nozzle part 726 may include a hose 7262, which is connected to the distribution pipe 736, and the nozzle 7261 which is connected to the hose 7262 and injects the liquid into a transport part 10 and a peripheral region. As the nozzle 7261 is connected to the liquid distribution pipe 736 through the hose 7262, a relative position of the nozzle 7261 with respect to a distal end of the distribution pipe 736 may change.

The nozzle 7261 may be disposed to be movable in the left and right direction. In order to enable this motion, the cleaning unit 70 may include a nozzle moving part 75. The nozzle moving part 75 may include a slider 753 coupled to the nozzle, and a cylinder part 752 to which the slider 753 is coupled. The cylinder part 752 may extend in the left and right direction and be disposed at a position spaced apart upward from each of transport stages. The cylinder part 752 may include a frame having a length fixed, and a piston capable of performing relative linear movement with respect to the frame in the left and right direction. As the slider 753 is coupled to the piston and moves linearly in the left and right direction, the nozzle 7261 coupled to the slider 753 may inject the liquid into the transport part 10 while moving linearly in the left and right direction. The cylinder part 752 may be a hydraulic cylinder that operates by pressure of liquid to be supplied, but the type thereof is not limited thereto.

The nozzle moving part 75 may further include a support 751. The support 751 may extend in the left and right direction and be disposed apart upward from the transport stage. The cylinder part 752 may be coupled to and supported by the support 751. The hose 7262 may be coupled to and supported by the support 751. Thus, a portion of the hose 7262 between one position, at which the hose 7262 is coupled to the support 751, and another position at which the hose 7262 is coupled to the liquid distribution pipe 736 may not be affected by the movement of the slider 753. However, another portion of the hose 7262 between the support 751 and the slider 753 may move when the slider 753 moves in the left and right direction.

The foregoing description of the nozzle 7261, the liquid distribution pipe 736, and so on, may apply to the various nozzles 722, 723, 724 and 725 and liquid distribution pipes 732, 733, 734 and 735 according to an embodiment of the present invention.

Heretofore, even though all components configuring the embodiments of the present disclosure are described to be combined as one unit or to operate as a combination thereof, the present disclosure is not limited to these embodiments. That is, within the scope of the present disclosure, all components may be selectively combined to one or more thereof to operate as a combination. The term such as "comprising," "configure", or "having", specifies the presence of components, unless there is a clearly different meaning in the present disclosure, but do not preclude the presence thereof and should be construed to further include other components. Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The description of the present invention is intended to be illustrative, and various changes and modifications can be made by those of ordinary skill in the art to which the present invention pertains, without departing from the spirit and scope of the present invention as defined by the appended claims. Therefore, the embodiments set forth herein are to describe the technical spirit of the present invention and not to limit. The scope of the technical spirit of the present invention is not limited by the embodiments. Moreover, the protective scope of the present invention should be determined by reasonable interpretation of the appended claims and all technical concepts coming within the equivalency range of the present application should be interpreted to be in the scope of the right of the present application.

The invention claimed is:

1. A food processing system comprising:
    a transport unit configured to continuously transport foods;
    a processing unit through which the transport unit passes and which is provided with an internal space in which the foods transported by the transport unit are processed; and
    a cleaning unit comprising a plurality of nozzles configured to inject liquid, which is any one of cleaning material and cleaning water, into the internal space so as to clean the interior of the processing unit, and a liquid supply module configured to selectively supply any one of the cleaning material and the cleaning water to the plurality of nozzles,
    wherein the processing unit comprises a first processing unit and a second processing unit, wherein one of a steaming unit, a cooling unit, a pre-freezing unit and a freezing part is the first processing unit, and the other is the second processing unit,
    wherein a flow rate of the liquid injected by a nozzle of the plurality of nozzles, which is disposed in the first processing unit, and a flow rate of the liquid injected by a nozzle of the plurality of nozzles, which is disposed in the second processing unit, are controlled to be independent of each other.

2. A food processing system comprising:
    a transport unit configured to continuously transport foods;
    a processing unit through which the transport unit passes and which is provided with an internal space in which the foods transported by the transport unit are processed; and
    a cleaning unit comprising a plurality of nozzles configured to inject liquid, which is any one of cleaning material and cleaning water, into the internal space so as to clean the interior of the processing unit, and a liquid supply module configured to selectively supply any one of the cleaning material and the cleaning water to the plurality of nozzles,
    wherein the internal space comprises a first space and a second space, which does not overlap the first space and is a space different from the first space,
    wherein the plurality of nozzles comprise a plurality of first nozzles disposed in the first space, and a plurality of second nozzles disposed in the second space, and
    a flow rate of the liquid injected by the plurality of first nozzles and a flow rate of the liquid injected by the plurality of second nozzles are controlled to be independent of each other.

3. The food processing system of claim 2, wherein the transport unit comprises a first transport stage and a second transport stage, which are disposed to be spaced apart from each other vertically,
    wherein the first transport stage is disposed in the first space, and the second transport stage is disposed in the second space.

4. The food processing system of claim 1, wherein each of the plurality of nozzles comprises a lower injector configured to inject the liquid downward.

5. The food processing system of claim 4, wherein each of the plurality of nozzles comprises an upper injector disposed above the lower injector and configured to inject the liquid therearound.

6. The food processing system of claim 5, wherein the lower injector is provided to inject the liquid at a pressure higher than a pressure at which the upper injector injects the liquid.

7. The food processing system of claim 5, wherein the upper injector comprises a plurality of upper injection holes through which the liquid is injected in a direction crossing a vertical direction,
    wherein directions in which the liquid is injected through the plurality of upper injection holes, respectively, are different from each other.

8. The food processing system of claim 5, wherein the upper injector comprises a rotary injector configured to inject the liquid therearound while rotating.

9. The food processing system of claim 1, wherein the liquid supply module comprises a pump configured to forcibly supply the liquid to the plurality of nozzles, and further comprises an inverter configured to adjust a pressure at which the pump forcibly supplies the liquid.

10. The food processing system of claim 1, wherein the cleaning material comprises at least one of steam, cleaning foam, sanitizer, or compressed air.

11. The food processing system of claim 10, wherein the liquid supply module supplies the liquid in order of the cleaning water, the cleaning foam, the cleaning water, the sanitizer, and the cleaning water, to the plurality of nozzles in a cleaning mode.

12. The food processing system of claim 11, wherein the food transported by the transport unit is frozen in a freezing space that is at least a portion of the internal space,
    wherein the liquid supply module supplies the compressed air to the plurality of nozzles disposed in the freezing space after the cleaning mode is performed.

13. The food processing system of claim 1, wherein the cleaning unit comprises:
    a slider coupled to the plurality of nozzles; and
    a nozzle moving part provided with a cylinder part coupled to the slider so as to allow the plurality of nozzles to move linearly.

14. A method for cleaning the food processing system of claim 1, the method comprising:
    injecting cleaning water into the internal space for removal of residues present in the internal space;
    injecting cleaning foam into the internal space;
    injecting the cleaning water into the internal space for removal of the cleaning foam;
    injecting a sanitizer into the internal space; and
    injecting the cleaning water into the internal space for removal of the sanitizer.

15. The food processing system of claim 2, wherein each of the plurality of nozzles comprises a lower injector configured to inject the liquid downward.

16. The food processing system of claim 15, wherein each of the plurality of nozzles comprises an upper injector disposed above the lower injector and configured to inject the liquid therearound.

17. The food processing system of claim 16, wherein the lower injector is provided to inject the liquid at a pressure higher than a pressure at which the upper injector injects the liquid.

18. The food processing system of claim 16, wherein the upper injector comprises a plurality of upper injection holes through which the liquid is injected in a direction crossing a vertical direction,
    wherein directions in which the liquid is injected through the plurality of upper injection holes, respectively, are different from each other.

19. The food processing system of claim 16, wherein the upper injector comprises a rotary injector configured to inject the liquid therearound while rotating.

\* \* \* \* \*